United States Patent
Canady

(10) Patent No.: US 7,549,990 B2
(45) Date of Patent: Jun. 23, 2009

(54) SURGICAL SCISSORS WITH ARGON PLASMA COAGULATION CAPABILITY

(76) Inventor: Jerome Canady, 1119 Jefferson St., McKeesport, PA (US) 15132

( * ) Notice: Subject to any disclaimer, the term of this patent is extended or adjusted under 35 U.S.C. 154(b) by 249 days.

(21) Appl. No.: 10/959,542

(22) Filed: Oct. 6, 2004

(65) Prior Publication Data

US 2005/0080413 A1    Apr. 14, 2005

Related U.S. Application Data

(60) Provisional application No. 60/509,343, filed on Oct. 7, 2003.

(51) Int. Cl.
*A61B 18/18* (2006.01)
(52) U.S. Cl. .............................. 606/45; 606/41; 606/49
(58) Field of Classification Search .................. 606/41, 606/45–52
See application file for complete search history.

(56) References Cited

U.S. PATENT DOCUMENTS

| | | |
|---|---|---|
| 4,040,426 A | 8/1977 | Morrison |
| 4,781,175 A | 11/1988 | McGreevy |
| 5,108,392 A | 4/1992 | Spingler |
| 5,122,138 A | 6/1992 | Manwaring |
| 5,207,675 A | 5/1993 | Canady |
| 5,217,460 A | 6/1993 | Knoepfler |
| 5,330,469 A | 7/1994 | Fleenor |
| 5,464,405 A | 11/1995 | Fujitsu |
| 5,542,945 A | 8/1996 | Fritzsch |
| 5,556,397 A | 9/1996 | Long et al. |
| 5,603,712 A | 2/1997 | Koranda et al. |
| 5,658,281 A | 8/1997 | Heard |
| 5,697,949 A | 12/1997 | Giurtino et al. |
| 5,720,745 A | 2/1998 | Farin et al. |
| 5,746,739 A | 5/1998 | Sutter |
| 6,149,620 A | 11/2000 | Baker et al. |
| 6,197,026 B1 | 3/2001 | Farin et al. |
| 6,231,574 B1 | 5/2001 | Posthuma |
| 6,283,963 B1 | 9/2001 | Regula |
| 6,293,946 B1 | 9/2001 | Thorne |
| 6,458,124 B1 | 10/2002 | Garito |
| 6,458,125 B1 | 10/2002 | Comescu |
| 6,464,701 B1 | 10/2002 | Hooven et al. |
| 6,558,379 B1 | 5/2003 | Batchelor et al. |
| 6,585,735 B1 | 7/2003 | Frazier et al. |
| 6,837,887 B2 * | 1/2005 | Woloszko et al. ............. 606/41 |
| 7,044,950 B2 * | 5/2006 | Yamamoto .................... 606/40 |
| 2002/0095152 A1 | 7/2002 | Ciarrocca |

* cited by examiner

*Primary Examiner*—Michael Peffley
(74) *Attorney, Agent, or Firm*—24IP Law Group; Timothy R. DeWitt

(57) ABSTRACT

Surgical scissors having argon plasma coagulation capability are shown. The surgical scissors include in their body a channel for receiving a flexible tube having a wire within it. The flexible tubing and wire within it are connected to a generator that provides electrical energy to the wire and argon or other inert gas to the tube. The flexible tubing travels a portion of the length of the scissors and ends with a coaxial connector in the proximity of the cutting edges of the scissors. An argon plasma coagulation sleeve is placed on the cutting end of one or both sides of the scissors and is connected to the flexible tubing and wire through the coaxial connector. Each sleeve has one or more ports for discharging electrified argon gas that coagulates tissue.

11 Claims, 5 Drawing Sheets

SURGICAL SCISSORS WITH ARGON PLASMA COAGULATION CAPABILITY

CROSS-REFERENCE TO RELATED APPLICATIONS

This application claims the benefit of the filing date of U.S. Provisional Application Ser. No. 60/509,343 entitled "Surgical Scissors with Argon Plasma Coagulation Capability," and filed on Oct. 7, 2003 by inventor Jerome Canady.

The above cross-referenced related application is hereby incorporated by reference herein in its entirety.

STATEMENT REGARDING FEDERALLY SPONSORED RESEARCH OR DEVELOPMENT

Not applicable.

BACKGROUND OF THE INVENTION

1. Field of the Invention

The present invention relates to surgical scissors which have argon plasma coagulation capability.

2. Brief Description of the Related Art

Controlling or arresting blood loss is of high priority during surgery so as to avoid or minimize the necessity of introducing foreign blood or blood products into a patient. This has increased in importance due to concern over contamination of the blood supply by viral agents which cause, for example, acquired immune deficiency syndrome (AIDS), hepatitis, and the like.

Standard means for controlling traumatic and surgical blood loss are electrosurgical generators and lasers, which respectively direct high-frequency electrical currents or light energy to localize heat in bleeding vessels so as to coagulate the overlying blood and vessel walls.

Argon beam coagulators additionally have been demonstrated to be effective tissue coagulators. Examples of argon beam coagulators for use in open surgery can be found in U.S. Pat. No. 4,040,426 to Morrison and U.S. Pat. No. 4,781,175 to McGreevy. Argon beam coagulators for use rigid and flexible endoscopy also are known. An example of a device for flexible endoscopy may be seen in U.S. Pat. No. 5,207,675 to the present inventor. In some embodiments in that patent, the inventor disclosed dual modality devices that could be used either for argon plasma coagulation or for traditionally electrocautery in an endoscopic environment. The inventor also disclosed an embodiment having the dual modality of argon plasma coagulation and endoscopic biopsy forceps. In that embodiment, argon plasma coagulation could be used by a surgeon while the biopsy forceps were withdrawn inside the flexible endoscopic tube. The biopsy forceps could then be extended and used, but argon plasma coagulation was not performed with the biopsy forceps extended from the end of the tube.

Surgical scissors have been known for many years. More recently, surgical scissors have been provided with electrosurgical capability such that the blades of the scissors may be used both to cut and to cauterize tissue. Electrosurgical scissors having both poles of electrosurgical energy exposed on the surface of the surgical blades have been referred to as "bipolar" electrosurgical scissors.

An example of bipolar electrosurgical scissors for use in open surgery can be found in U.S. Pat. No. 5,658,281, which is hereby incorporated by reference. An open surgery embodiment of U.S. Pat. No. 5,658,281 is shown in FIG. 1. Bipolar scissors 10 has first and second shearing members 11 and 12, as shown in FIG. 1. The shearing members 11 and 12 are connected by a pivoting joint 13 to allow scissors-like motion of the shearing members 11 and 12. Each shearing member 11 and 12 has a distal end 14 and a shearing surface 15 located between the pivoting joint 13 and the distal end 14. The distal ends 14 of the shearing members 11 and 12 are the ends designed to contact tissue. Each shearing surface 15 is bounded on one side by a cutting edge 16. Each shearing member 11 and 12 also has an exterior surface 17. The exterior surfaces 17 are the portions of each shearing member 11 and 12 which are exposed when the shearing members 11 and 12 are in a closed, or mated position. The exterior surfaces 17 are generally opposite the shearing surfaces 15 on each shearing member 11 and 12.

Electrical connections 19 are located on the scissors 10 for receiving two poles 20 and 21 of bipolar electrosurgical energy. The electrosurgical energy is high-frequency electrical energy, and thus the two poles 20 and 21 are referenced as a first pole 20 and a second pole 21, respectively. The electrical connections 19 receive the two poles 20 and 21 from an electrosurgical generator. The two poles 20 and 21 are then conducted to different regions on the surgical scissors 10. The arrangement of the different conductive regions 22 makes the bipolar scissors 10 more useful to surgeons than previous designs. In particular, the conductive regions 22 are positioned on the shearing members 11 and 12 such that both poles 20 and 21 are exposed to tissue on each shearing member 11 and 12, even when the scissors 10 are in a closed position. In an alternative embodiment of FIG. 1, the shearing surfaces 15 are each conductive, as shown in FIG. 2. The two shearing surfaces 15 meet during use, and therefore both shearing surfaces 15 are electrically connected to the same pole 20 to avoid an electrical short circuit. In this embodiment, the pivoting joint 13 does not need to be electrically insulated.

A second example of bipolar surgical scissors can be found in U.S. Pat. No. 6,283,963, which is hereby incorporated by reference. In a first embodiment of the bipolar electrosurgical scissors in that patent, the electrical insulation extends into the first and second cutting blades such that ⅓ of their distal tip is uninsulated. In a second embodiment of the bipolar electrosurgical scissors of that patent, the electrical insulation extends into the first and second cutting members such that they are entirely insulated except for their corresponding cutting edges.

Laparoscopic embodiments of bipolar surgical scissors also are known. Examples of such embodiments can be seen in U.S. Pat. Nos. 5,658,281 and 6,464,701. A laparoscopic embodiment of bipolar surgical scissors from U.S. Pat. No. 5,658,281 is shown in FIG. 2.

The present invention provides dual or trimode capabilities for surgical scissors such that the dual mode surgical instrument can be used simply to cut tissue, simply to coagulate tissue via argon plasma coagulation, or can be used to simultaneously cut tissue and to coagulate tissue via argon plasma coagulation. A trimodal embodiment provides the user with the flexibility to cut tissue and coagulate tissue either via argon plasma coagulation or via traditional electrocautery.

SUMMARY OF THE INVENTION

Surgical scissors having argon plasma coagulation capability are shown. The surgical scissors include in their body a channel for receiving a flexible tube having a wire within it. The flexible tubing and wire within it are connected to a generator that provides electrical energy to the wire and argon or other inert gas to the tube. The flexible tubing travels a portion of the length of the scissors and ends with a coaxial connector in the proximity of the cutting edges of the scissors. An argon plasma coagulation sleeve is placed on the cutting end of one or both sides of the scissors and is connected to the flexible tubing and wire through the coaxial connector. Each sleeve has one or more ports for discharging electrified argon gas that coagulates tissue.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention.

Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRITION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1:
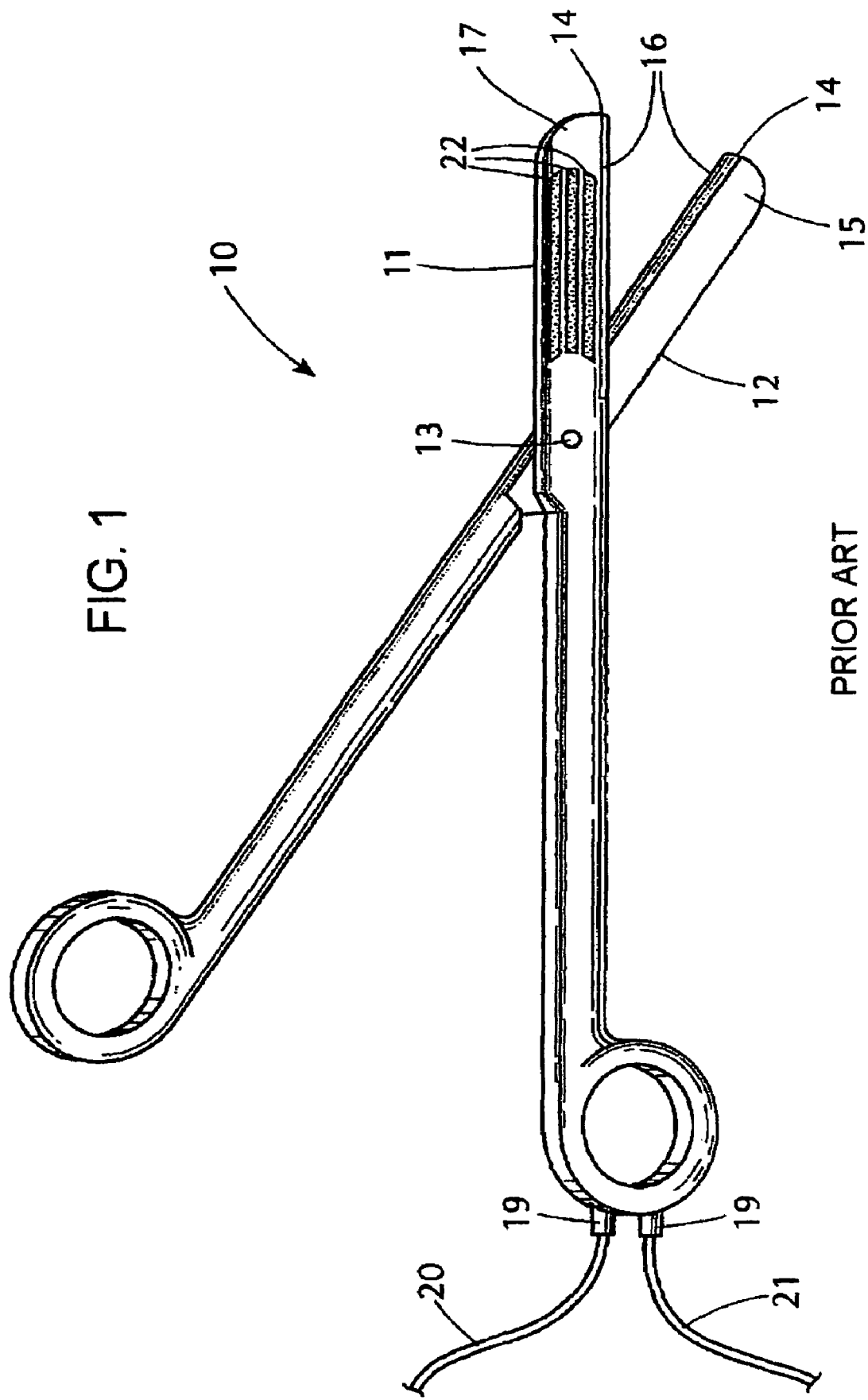
FIG. 1 illustrates a prior art bipolar surgical scissors.
Figure 2:
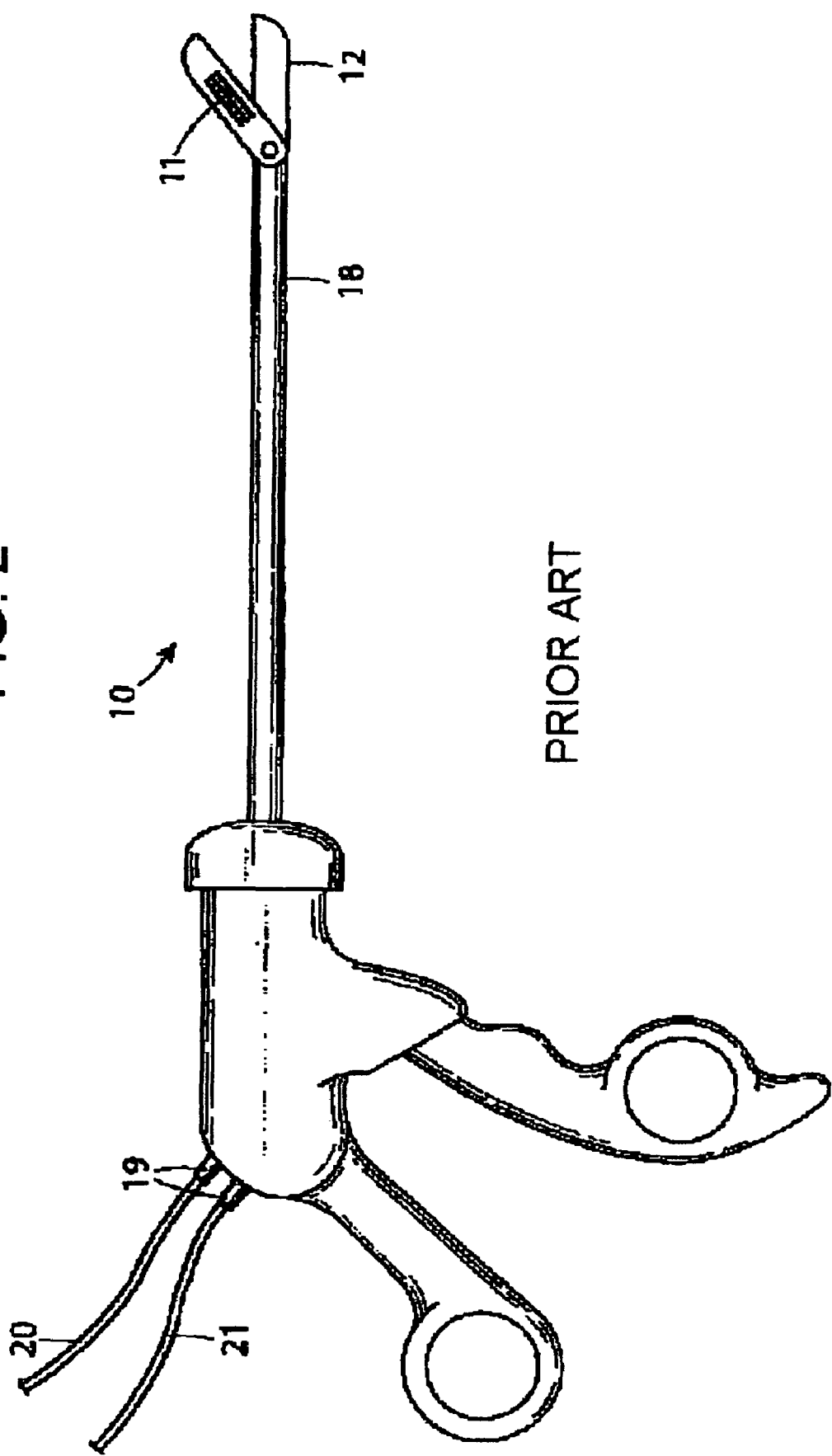
FIG. 2 illustrates a prior art laparoscopic bipolar surgical scissors.
Figure 3:
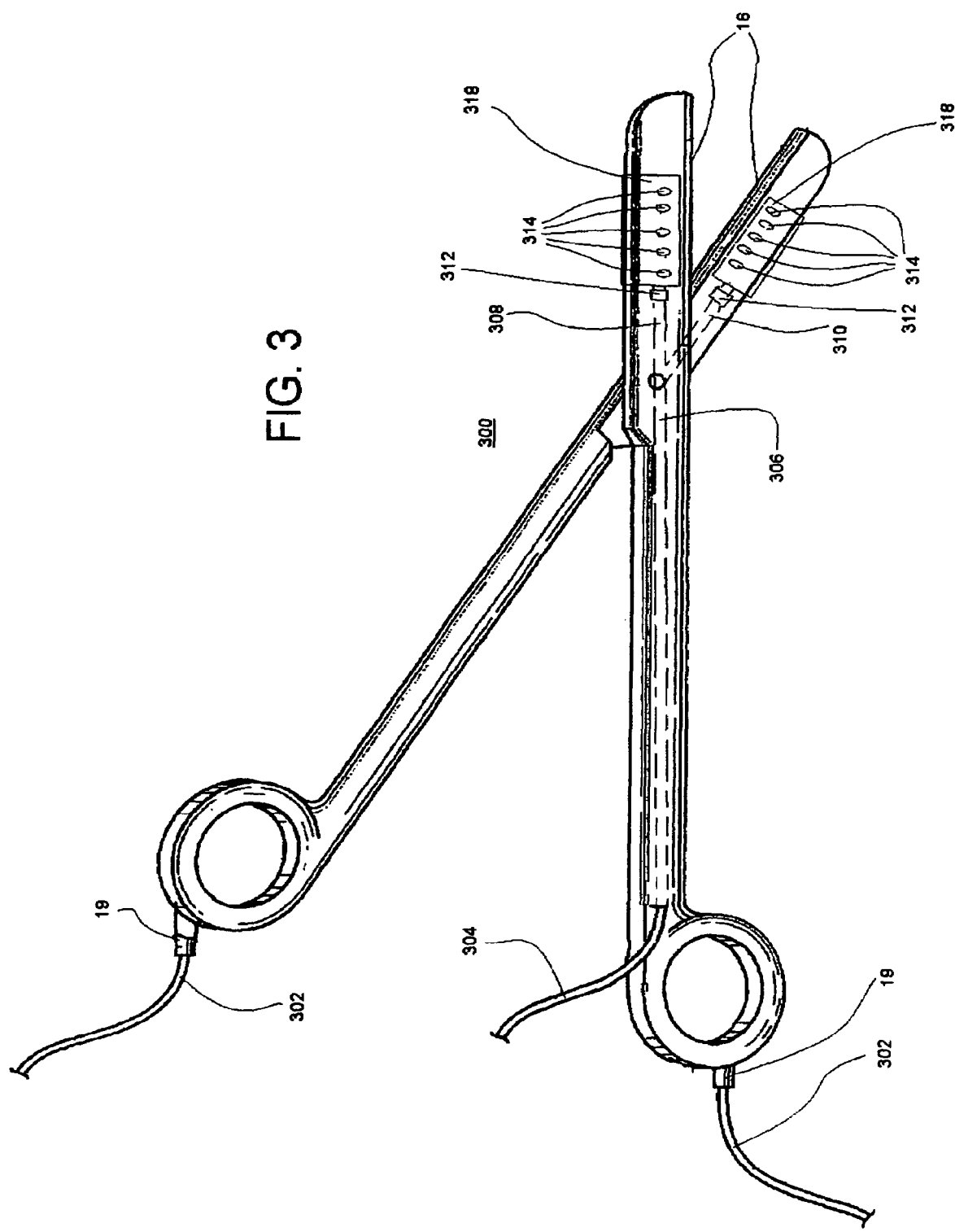
FIG. 3 illustrates a side view of a preferred embodiment of the invention.

Referring to FIG. 3, a preferred embodiment of the surgical scissors 300 with argon plasma coagulation capability is shown. The surgical scissors have two sides, each having a cutting surface 16. The two sides of the scissors have conventional bipolar connectors 19 for connecting the scissors to a generator (not shown) through leads 302. The scissors of the preferred embodiment shown in FIG. 3 include a channel 306 that receives a flexible APC tube 304 that splits into tubes 308 and 310 in this embodiment for providing APC to the two sides of the scissors. Other embodiments in which the tube 304 is connected to some portion of the scissors via other means such as by one or more clips, snaps, or even by glue will be apparent to one of skill in the art.

The flexible tubes 304, 308, and 310 each include within them a wire for conducting electrical energy. The tube 304 connects at its proximal end to a source of argon or other inert gas and to a source of electrical energy such as a generator.

The tubes 308 and 310, and the respective wires within them, include at their distal ends coaxial connectors 312 that connect to APC sleeves 318. Each sleeve includes within it an APC tube having within it a wire for conducting electrical energy. Each sleeve includes one or more ports 314 for discharging electrified argon gas. Each sleeve 318 may have ports 314 for discharging electrified argon gas on one or both sides of each side of the surgical scissors. When the sleeves are mounted on the blades, it is preferable that the argon ports or wells are 1 to 4 millimeters from the cutting edges of the scissors and most preferably the well ports are approximately 2 millimeters from the cutting edges of the scissors.

During surgery, a surgeon can use the surgical scissors of the present invention in three different ways: (1) for cutting tissue with edges 16; (2) for coagulating tissue with argon plasma coagulation; and (3) for cauterizing tissue through traditional bipolar cauterization. The surgeon may use combinations of those three, such as coagulating or cauterizing tissue while cutting the tissue with edges 16. The surgeon also may use a combination of argon plasma coagulation (APC) and bipolar electrocauterization.

The sleeves can be placed onto or mounted to the scissors in a variety of different ways and can be formed from a variety of different materials. The sleeves could be composed of a flexible material similar to the material used for the APC tubing, in which case they may be affixed to the scissors via an adhesive or a retaining clip. The sleeves alternatively could me made form a hard plastic material such that then could be slid onto or clipped onto the sides of the scissors. The structure of the ports 314 additionally could be formed as an integral part of the scissors, in which case they would not be part of a sleeve but rather would be one or more channels in the scissors. The sleeve embodiments, however, allow for inexpensive manufacturing of disposable components, such as the sleeves 318 and the tubing 304.

Figure 4:
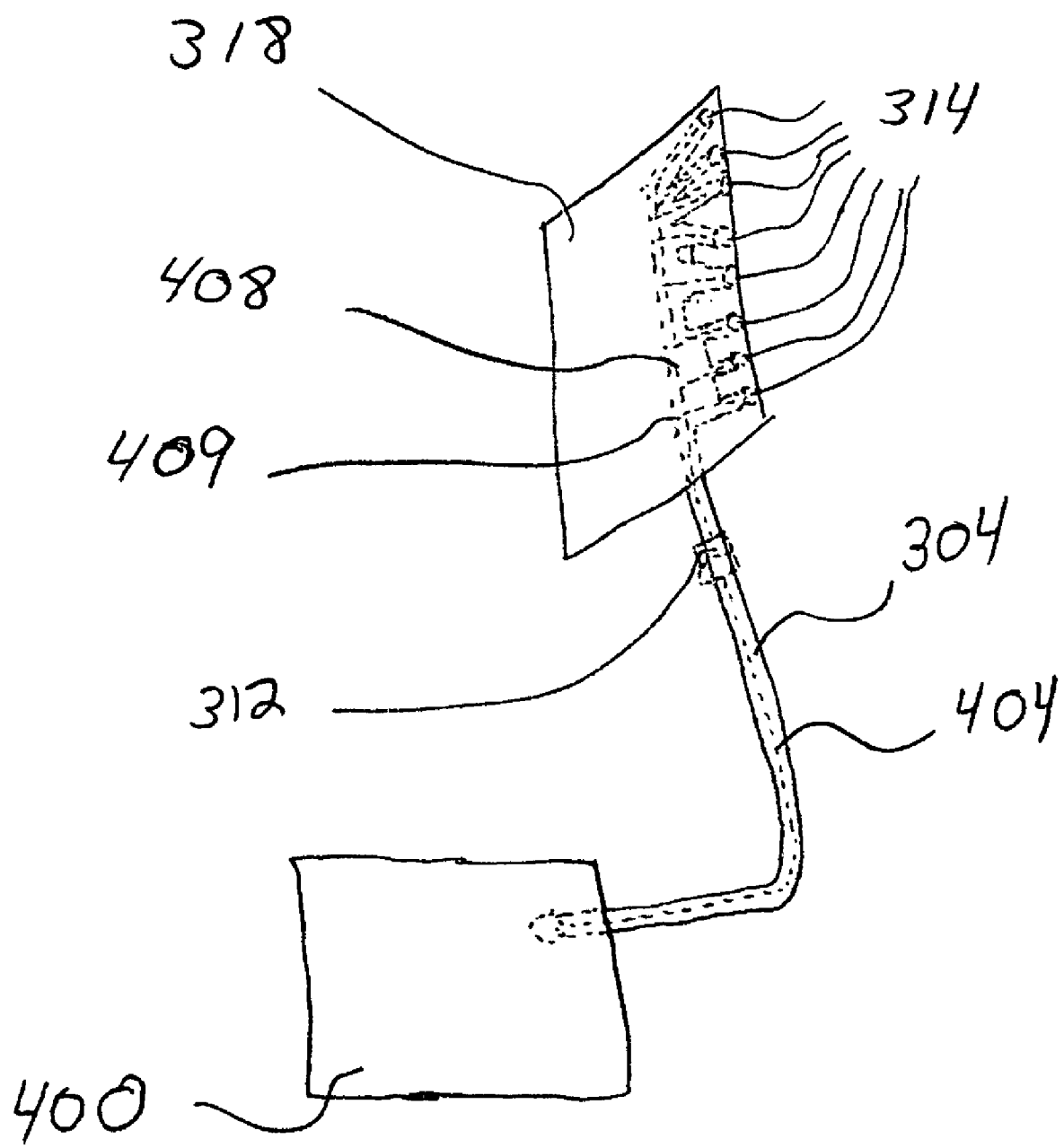
FIG. 4 illustrates an argon plasma coagulation sleeve in accordance with a preferred embodiment of the invention.

FIG. 4 illustrates an embodiment of a disposable sleeve 318 that can be attached to the sides of the surgical scissors. The sleeve includes one or more ports 314, a tube 408 having within it a wire 409. The tube 408 and wire 409 have a connector 312 for ultimately connecting, typically through a tube 304 having a wire 308 within it, to sources of an inert gas such as argon and a source of electrical energy such as a generator 400.

Figure 5:
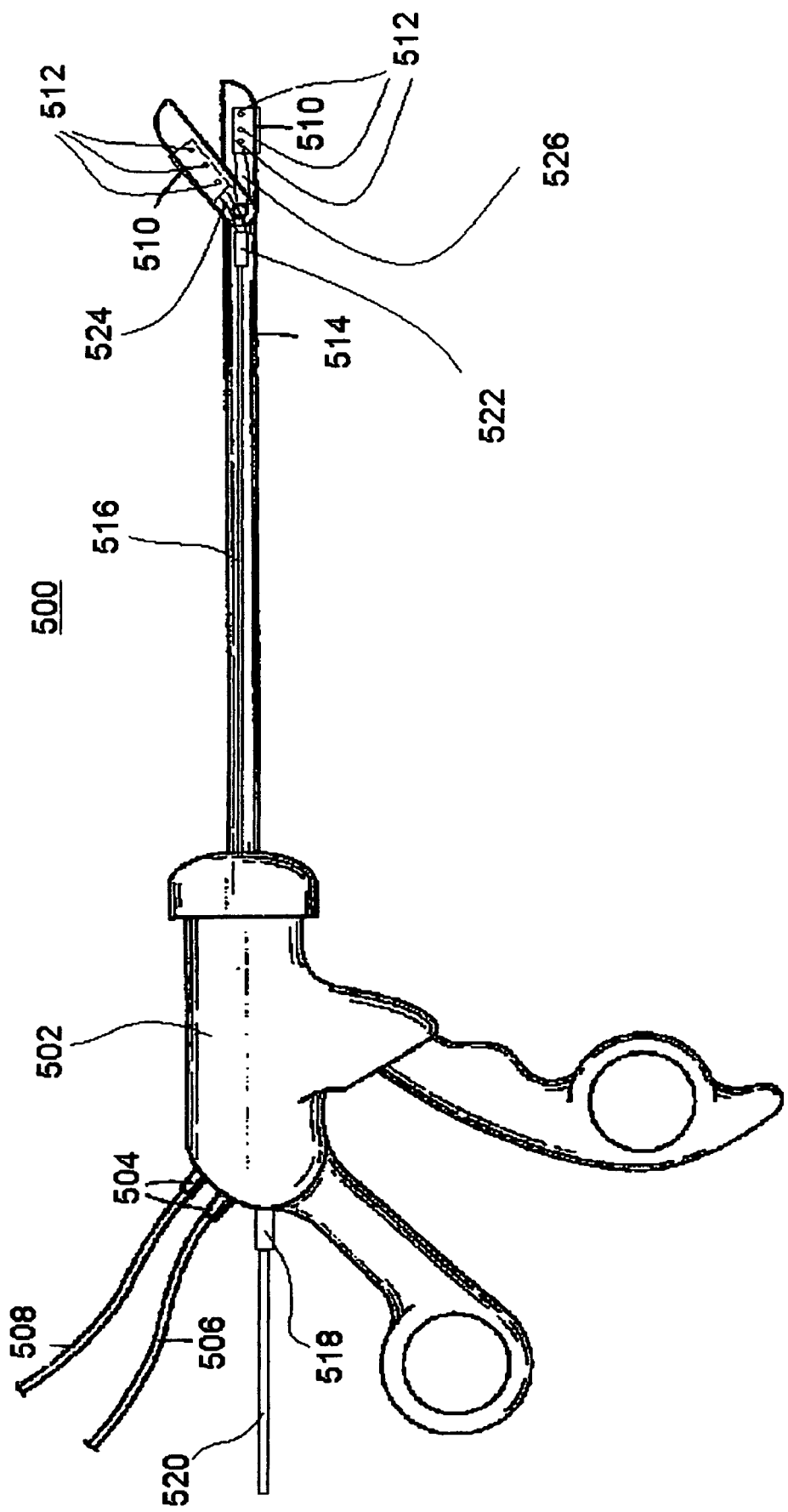
FIG. 5 illustrates a laparoscopic embodiment of the present invention.

FIG. 5 illustrates a laparoscopic embodiment of the present invention. The laparoscopic scissors have a housing 502 having connectors 504 for connecting wires or tubes 506, 508 to a generator. The housing further has a coaxial connector 518 and tube 520 for connecting to a source of argon or other inert gas. A rigid hollow stem 516 extends from the housing 502 and has attached to its distal end a pair of scissor blades. Conventional means for manipulating the scissors blades may be used.

In a preferred embodiment, a tube 516 with a wire within it extends inside the stem or inside a channel in the stem and has a bipolar connector 522 at its distal end. In an alternative embodiment, the tube 516 may extend down the outside of the stem and may be affixed to the stem in a variety of different ways such as by glue, an adhesive, or by one or more clips. Tubes 524 and 526 extend from an opposing connector to APC sleeves or housings 510. Each APC sleeve has one or more wells or ports for discharging argon or another inert gas.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. Surgical scissors comprising:
   a first member having a first cutting surface;
   a second member having a second cutting surface;
   at least one channel within said first member;
   a wire within said at least one channel, said wire having a distal end;
   a port in said at least one channel;
   a connector for connecting said at least one channel to a source of an inert gas;
   wherein said distal end of said wire is within approximately 4 mm of said port.

2. Surgical scissors according to claim 1 wherein said at least one channel comprises flexible tubing.

3. Surgical scissors according to claim 1 further comprising a tungsten tip at said distal end of said wire.

4. Surgical scissors according to claim 1 wherein said distal end of said wire is approximately 1 mm from said port.

5. Surgical scissors according to claim 1 further comprising a plurality of channels within said first member, each of said plurality of channels terminating at a port and means for connecting said plurality of channels to a source of an inert gas.

6. Surgical scissors according to claim 1 wherein said inert gas comprises argon.

7. Surgical scissors according to claim 1 further comprising a connector for connecting said wire to a source of RF energy.

8. A surgical apparatus comprising:
   a body having a proximal end and a distal end;
   a pair of surgical scissors near a distal end of said body, said pair of surgical scissors having a first cutting surface and a second cutting surface;
   a channel extending along a length of said body and through a substantial portion of said first cutting surface;
   a wire within said channel, said wire having a distal end;
   a port at a distal end of said channel; and
   a connector for connecting said channel to a source of an inert gas.

9. A surgical apparatus according to claim 8 further comprising:
   means for electrifying said first and second cutting surfaces of said surgical scissors.

10. A surgical apparatus according to claim 8 further comprising:
    means for connecting said wire to a source of RF energy.

11. A surgical apparatus according to claim 8 wherein said inert gas comprises argon.

* * * * *